United States Patent [19]
Bertelsen et al.

[11] Patent Number: 5,431,061
[45] Date of Patent: Jul. 11, 1995

[54] DEFLECTION TESTING FIXTURE ASSEMBLY AND METHODS OF TESTING

[75] Inventors: William D. Bertelsen, Vassar; Robert H. Monroe, Bay City, both of Mich.

[73] Assignee: Gougeon Brothers, Inc., Saginaw, Mich.

[21] Appl. No.: 26,609

[22] Filed: Mar. 5, 1993

[51] Int. Cl.$^6$ ............................................. G01N 3/20
[52] U.S. Cl. .................................................. 73/852
[58] Field of Search ................ 73/852, 853, 851, 849, 73/825, 850, 854

[56] References Cited

U.S. PATENT DOCUMENTS

| | | |
|---|---|---|
| 358,056 | 2/1887 | Mullen . |
| 924,625 | 6/1909 | Putnam . |
| 1,445,963 | 2/1923 | LaBatt et al. . |
| 2,404,584 | 7/1946 | Liska et al. . |
| 2,864,253 | 12/1958 | Lenton . |
| 3,760,636 | 9/1973 | Serry ..................................... 73/852 |
| 3,975,950 | 8/1976 | Erdei . |
| 4,589,288 | 5/1986 | Porter et al. . |

OTHER PUBLICATIONS

Publication stated by the author Craig Riley to have occurred in 1987 or prior thereto entitled "Structural Suitability Of ±45 Degree Fiberglass Laminates For Use In Marine Applications".
Publication Jun. 19, 1989—Sandwich Constructions 1 by Olsson and Reichard.

*Primary Examiner*—Hezron E. Williams
*Assistant Examiner*—Nashmiya Ashraf
*Attorney, Agent, or Firm*—Learman & McCulloch

[57] ABSTRACT

A testing fixture for investigating the effects of pressure loadings on marine hull and other plate panels in a testing machine includes a liquid-filled bladder adapted to be received on the machine platen, a fixture supported by the machine frame incorporating edge movement restraint members for receiving the panel to be tested and contacting it around its perimetrical edge on both sides, and a measuring element supported by the fixture for measuring the deflection of the panel as the bladder is moved with the platen and pliantly conforms to the surface of one side of the panel to apply a distributed load imposing a bend in the panel inboard of its restrained edges in two dimensions along two axes simultaneously over a substantial area of its surface.

11 Claims, 6 Drawing Sheets

DEFLECTION TESTING FIXTURE ASSEMBLY AND METHODS OF TESTING

FIELD OF THE INVENTION

This invention relates to a novel testing method and a novel fixture assembly for a testing machine having a frame mounting a deflection measuring device opposite a platen, which is relatively movable with respect to the frame mounting the measuring device, for investigating the effects of various pressure loadings on marine hull and other plate panel specimens.

BACKGROUND OF THE INVENTION

There has been a long term need for a better method of testing sandwich composites of the type used in applications such as in marine hulls, where the material must withstand loads which apply bends in the panel in two dimensions along two axes simultaneously over a substantial area of surface. While sandwich composite materials offer the potential to build structures which are lighter and stronger than ever before, there is a need for a practical standard test regimen that can realistically evaluate new hull composites and compare them with more traditional materials such as wood strip planking and marine plywood. There is a need for reliable data on the strength and durability of various materials which are contemplated for use by modern marine designers, and which must be considered by insurers and regulatory agencies.

In marine applications, particularly, unbacked expanses of sandwich composite materials are subjected to long term pressure loads or hydrostatic loading from the bodies of water in which they float. As propulsion takes place and waves are encountered, hydrodynamic loads are superimposed on the hull, and these loads induced by surface travel are repetitive and difficult to analyze. Because a typical hull is braced by intersecting bulkheads and stringers which form a lattice supporting the hull sheath, there are rectangular expanses of hull sheath spanning the interstices which are not directly braced, and water pressure forces these unsupported areas to bulge inwardly to some degree. Sandwich composites suitable for marine applications must be sufficiently stiff to resist the forces tending to bend the non-backed expanses in two dimensions along two axes simultaneously. Because bi-directional bending is involved, simple bending beam tests are not of great value in predicting the ultimate strength of the material or gauging sensitivity to visco-elastic effects, including time dependent phenomena such as creep rupture and fatigue. Particularly because such sandwich composites are nonhomogeneous and anisotropic, simple bending-beam tests do not recreate the complex interactions between resin, fiber, and core that take place when a flat composite panel is forced to compoundly bend.

In the past, too many hulls have been designed on the basis of static beam tests for flexural stiffness and, further, without recognition of the repeated decline in rigidity caused by repeated loads in the nature of fatigue cycles. This recognition is important in modern hull engineering, particularly with nonhomogeneous anisotropic materials.

For a number of years, various tests have been conducted on an MTS testing machine wherein a load measuring device or load cell is provided on an overhead crosshead, and a hydraulically operated platen is movable upwardly in this testing. Applicants' assignee has utilized a pyramidal plywood fixture carried by the load cell which had an open lower end of square configuration against which the test panel was pressed by a platen applied load transmitted to the lower surface of the test panel. A measuring device to effect the degree of bend applied to the specimen panel by the load was carried by the fixture, but difficulty was encountered in applying the contact load to obtain a better load distribution over the contact area. Feeling that it would be more appropriate to use hydrostatic pressure in the testing of hull materials, a water filled bladder was developed which could be supported on the platen and moved to bend the panel in the test. Such a bladder allowed significant panel deflection to take place while maintaining excellent load distribution. While the fixture assembly proved to be a useful tool for broad comparisons, it was not suitable for evaluations of a precise character because the edges of the panel projected beyond the pyramidal fixture and the corners of the panel tended to be displaced as a result of the bending load applied by the bladder.

SUMMARY OF THE INVENTION

The present invention is concerned with a support system carried by the pyramid fixture for preventing the corners of the panel from being moved by the bending stresses out of the original plane. It has been determined that without zero edge displacement, shear stress measurements in the core, as a result of the compound bending load, cannot be accurately tested.

One of the prime objects of the present invention is to design a fixture having a panel edge restraint system which insures zero edge displacement of the test panel edges, and provides the qualitative testing necessary in marine hull design considerations, for example.

The invention is concerned with an assembly of components which includes the previously mentioned self-contained, liquid filled bladder, the edge restraint assembly connected with the load measuring device which incorporates edge movement restraint journal frames for receiving the panel to be tested, and the measuring device which measures the deflection of the panel as the bladder is moved with the platen and flattens to apply a distributed load to the panel imposing a bend in the panel in two dimensions along two axes simultaneously.

A further object of the present invention is to design a fixture system for testing apparatus of the type described which enables investigation of the effect of static and repeated constant stress pressure loads on a broad spectrum of sandwich composites, as well as other materials.

Another object of the invention is to design a system and method of the character described which can be used for considering the effects of fatigue, as well as ultimate strength.

Still another object of the invention is to design a system of the character described wherein the specimen panel is restrained at its edges so that center bulging of the panel is not affected by edge movement.

Still another object of the invention is to provide a system of the character described wherein loading and unloading of the panel before and after the test is an easy task, and can be accomplished relatively easily and rapidly.

Still another object of the invention is to provide a testing system which promotes the uniformity of testing with panels of different type, since, with the edge restraint system which has been devised, the different propensity for various panels to move off during pressure loading is not a variable which affects the test.

Other objects and advantages of the invention will become apparent with reference to the accompanying drawings and the accompanying descriptive matter.

DESCRIPTION OF THE PREFERRED EMBODIMENT

Figure 1:
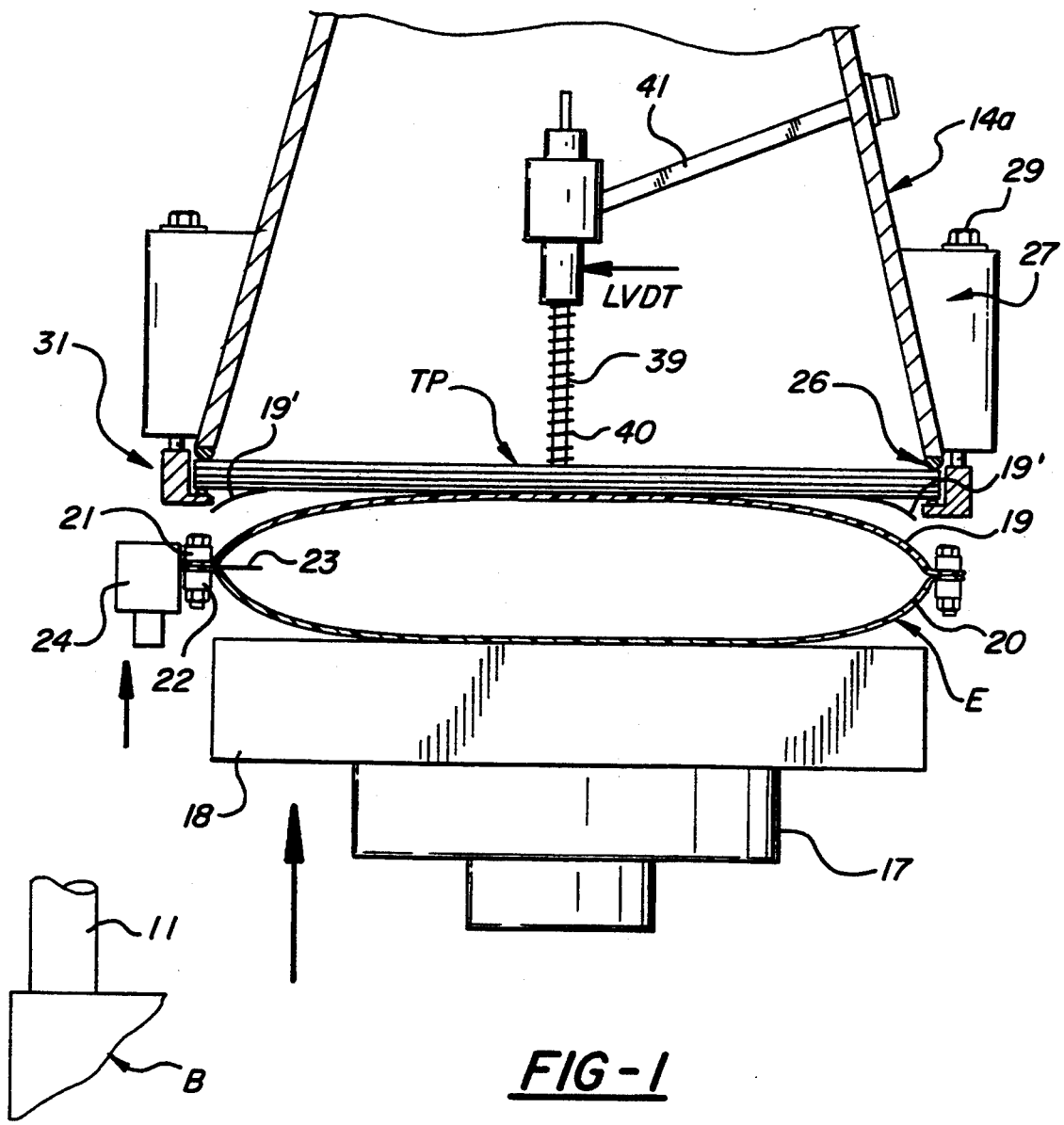
FIG. 1 is a fragmentary, schematic, sectional elevational view illustrating our testing fixture system.
Figure 2:
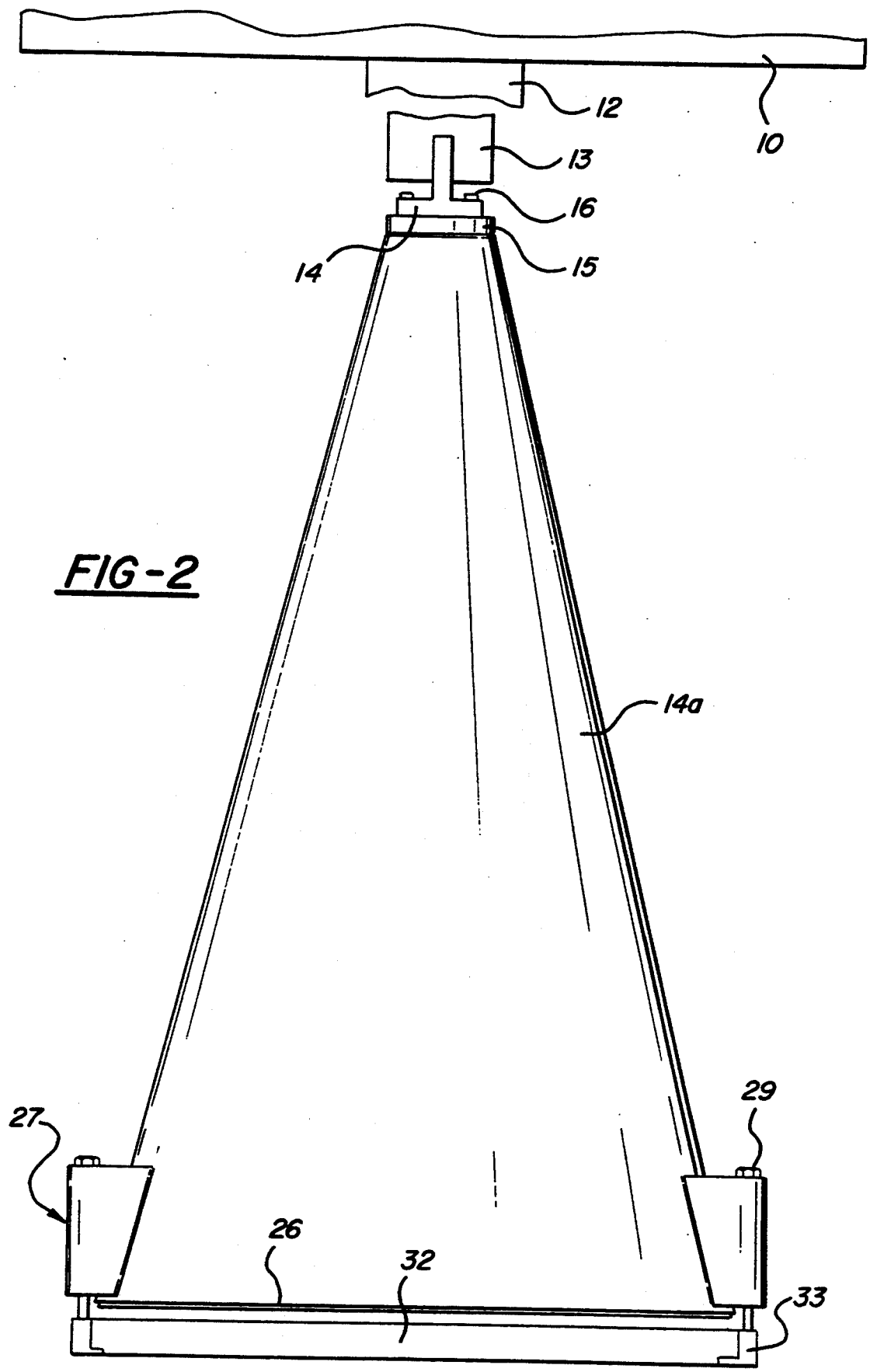
FIG. 2 is a fragmentary, schematic, elevational view, with portions of the testing machine shown only schematically.

Referring now more particularly to FIGS. 1 and 2, it is to be appreciated that the fixture assembly of the invention is employed in a testing machine of the type, for instance, marketed by MTS Systems Corporation of Minneapolis, Minn. Its model 810 machine includes an upper crosshead 10 supported on vertically disposed posts or columns 11 extending to the base B of the machine. The crosshead 10, in such a machine, is capable of vertical movement, but can also be used in vertically stationary position, as in the testing procedure to be described.

As FIG. 2 indicates, a load cell 12 connected to frame element or crosshead 10 has hydraulic grippers 13 for gripping and supporting a T-member 14. A hollow pyramidal fixture 14a, of square cross-section throughout its vertical extent, has a cap 15 bolted to the T-member 14 as at 16. The fixture 14a is supported directly above the MTS machine actuator plate 17 which is hydraulically powered by the MTS machine to move upwardly at a controlled rate toward the load cell 12.

The actuator 17 is supported for vertical movement in any acceptable manner by the base B and a support block 18 is provided on the actuator 17 to receive a bladder or envelope, generally designated E, of square configuration. The bladder or envelope E is formed of an upper and a lower square membrane section, 19 and 20 respectively, whose perimetral edges are clamped by upper and lower square frames made up of end and side rails 21, and end and side rails 22. The upper and lower rails 21 and 22 are tightly bolted together by bolts 21a and nuts 22a (FIG. 3) so that no leaks can occur when the envelope E is filled with water or another incompressible liquid. The ends of rails 21 and 22 abut and tightly fit together.

The membrane members 19 and 20 may be formed of food service, polyester belting. This belting comprises a polyester fabric embedded in a nitrile, polyvinyl chloride material forming a sheath for the fabric, and may be characterized as both pliant and moderately stretchable or elastic.

At one side of the envelope E, a probe 23 extends into the interior of the envelope E, from a pressure sensor device 24. The pressure sensor 24 may be an "Omega" pressure transducer of the type having a pressure sensitive diaphragm with a strain gauge bonded to it, which can be obtained from Omega Engineering Inc. of Stamford, Conn. As shown particularly in FIGS. 2 and 3, the lower end of each sidewall of the square in cross-section fixture 14a is provided with a channel-shaped, steel, lower edge member 25 for housing a steel rod 26. The steel rods 26 on each sidewall 14a are mitred to meet in abutting relation and form a continuous square journal frame against which a test panel TP may be pressed during the test.

Figure 4:
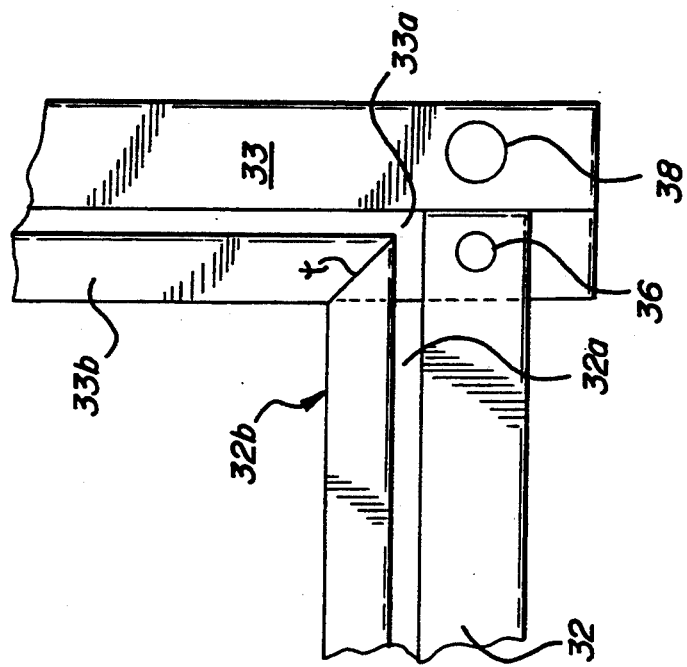
FIG. 4 is a fragmentary, enlarged, plan view of the lower edge restraint frame.
Figure 5:
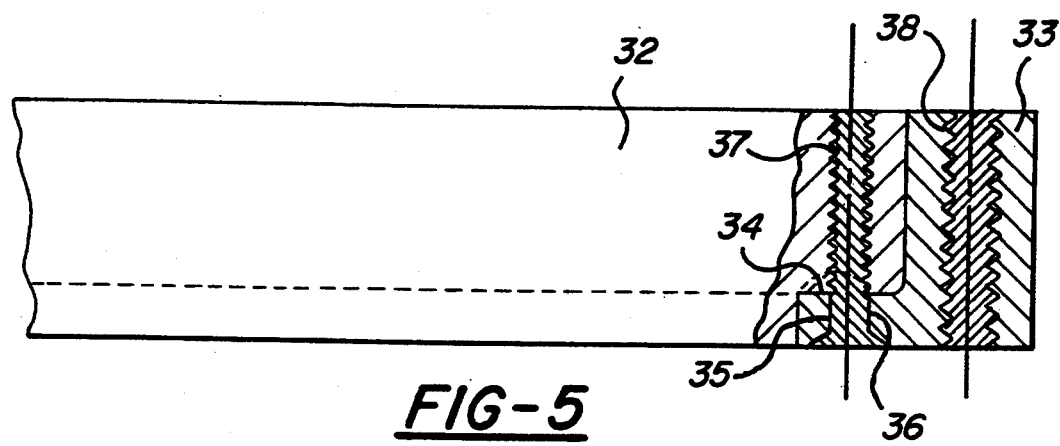
FIG. 5 is a fragmentary, side elevational view thereof.
Figure 6:
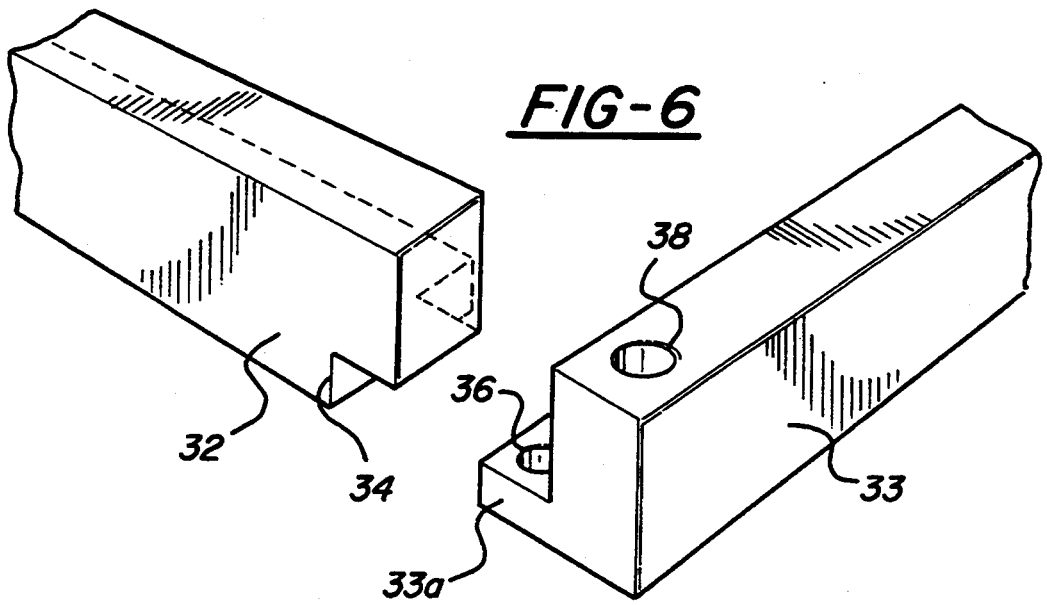
FIG. 6 is a fragmentary perspective view illustrating the manner in which the rails of the lower restraint frame interfit.

Provided on the sidewalls of the fixture 14a, at the corners, are anchor blocks, generally designated 27, having vertically extending openings 28 for receiving elongate bolt members 29 which bear on washers 30. An under, or lower, journal frame assembly, generally designated 31, consists of side and end rail members, 32 and 33, respectively, which it will be observed in FIG. 6 are interfitted and joined to provide a square support frame for the test panel TP. The steel rail members 32 and 33 are each formed with projecting lips or flanges, 32a and 33a respectively, for supporting curvilinear metal bead rails, 32b and 33b respectively, which are cut on a bias, or mitred, as shown at x in FIG. 4 at each of their ends so as to join and form a continuous square lower journal frame on which a test panel TP is supported. The side and end members 32 and 33 interfit, as particularly illustrated in FIGS. 5 and 6, where it is to be noted that the side members 32 are notched as at 34 so as to fit over the flange 33a. Screws 35 may be threaded through openings 36 in the flanges 33a and received in threaded openings 37 provided in the members 32 to secure the members 32 and 33 in tightly assembled position. Also provided in the members 33 at their ends, are threaded openings 38 into which the bolts 29 thread to permit the lower journal frame assembly 31 to be moved upwardly with respect to the rod journals 26, and also to permit the lower edge support frame assembly 31 to be completely removed from the upper journal frame when it is desired to remove the test panel TP and substitute another one.

As FIG. 1 indicates, a linear variable differential transformer LVDT is provided with a core probe 39 which is normally maintained in extended position by a spring 40. The LVDT unit may be a "Schaevitz" device manufactured by Lucas Schaevitz Company of Pennsauken, N.J. which produces an electrical output proportional to the displacement of the core 39. The LVDT unit includes a primary coil energized by an external alternating current source. It also includes two secondary coils with the core inside the coil assembly to provide a path for the magnetic flux linking the coils. With voltages induced in the two secondary coils when the primary coil is energized and the two secondary coils connected to be of opposite polarity, the output of this transducer is the difference between these voltages, which is zero when the core is at the center or null position shown in FIG. 1, before the actuator 17 is moved upwardly to bulge the test panel TP. When the core 39 is moved from the null position, the induced voltage in the one secondary coil toward which the core is moved increases, while the induced voltage in the opposite secondary coil decreases, and this movement produces a differential voltage output signal that varies linearly with changes in core position.

As FIG. 1 indicates, the LVDT device may be supported by a bolt or bolt members 41 in a central or axial position within fixture 14a, such that the core 39 is in engagement with the very center of the test panel TP.

Figure 7:
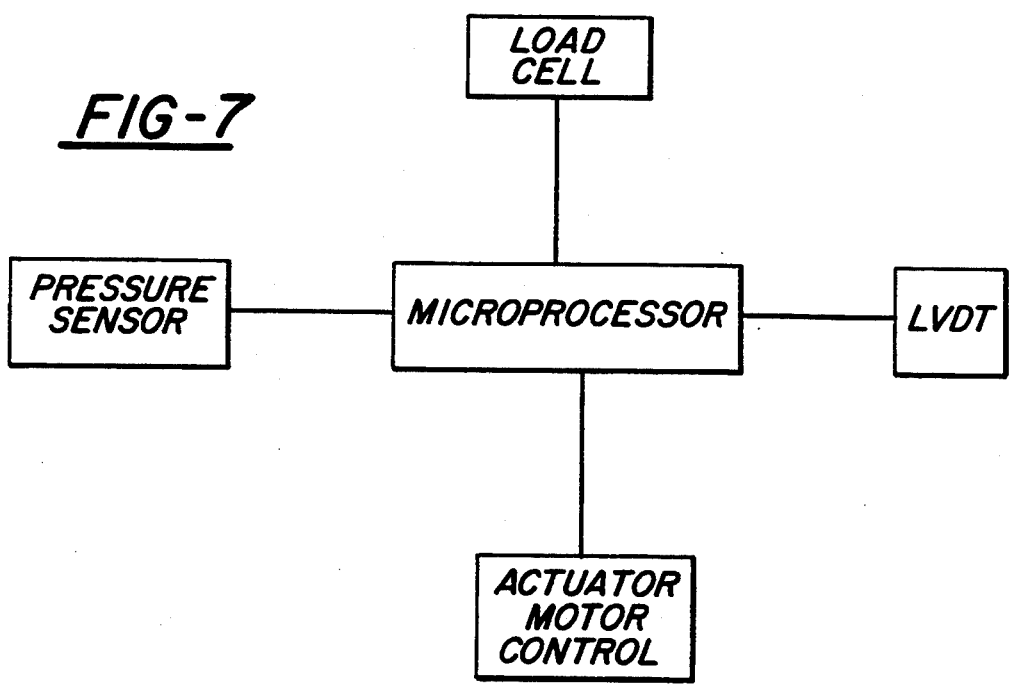
FIG. 7 is a schematic diagram identifying electronic components used in the test.

FIG. 7 is a block diagram portraying the various electronic units which are commonly employed in the commercially available MTS testing system. The signals from the pressure sensor 24, the LVDT device and the load cell 12 are fed to the MTS machine controller/computer, which further controls the hydraulic motor for raising the actuator 17 at a controlled rate of speed. The computer is a microprocessor having an operating console. A motor-pump assembly drives actuator plate 17 via a cylinder which is under closed-loop servo-hydraulic control in the MTS machine identified. In such systems, a control signal such as a ramp function or cyclic wave form, is generated from a program source like a computer, function generator or ramp generator, and the controller takes this signal and converts it to a control signal which causes movement of the actuator plate 17 to apply a load which is transmitted to the load cell by the fixture 14a. This load is measured through the precision transducers of the load cell with the controller comparing input from the programmer to output from the transducer to make sure both are the same, and thereby guarantee accuracy of both the load and the rate required to get to it.

The computer is programmed to permit high cycle fatigue tests to be performed as well. The sinusoidal wave forms are produced by a function generator.

Figure 8:
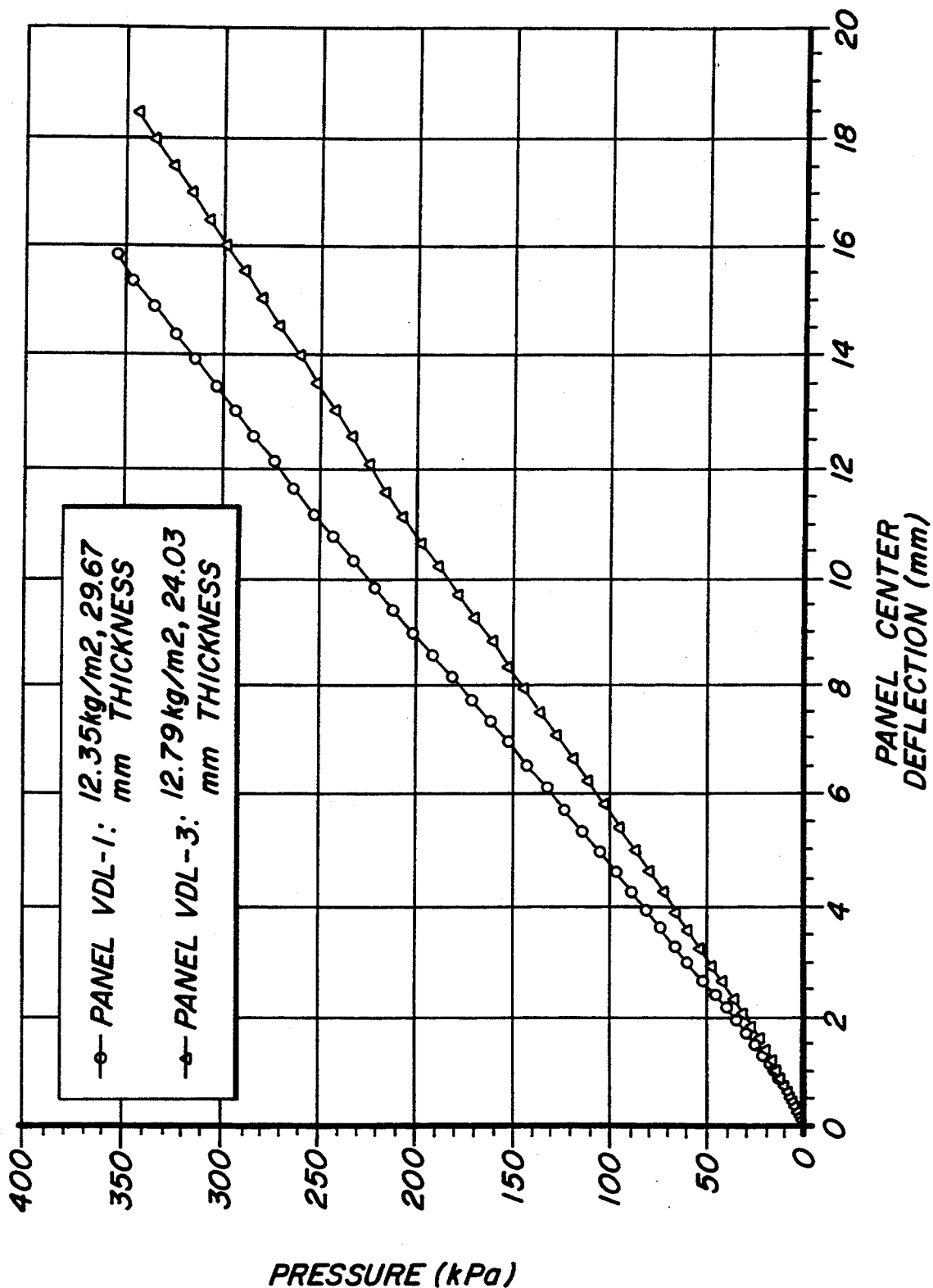
FIG. 8 is a typical graph which considers panel center deflection to the point of failure.

FIG. 8 illustrates the bladder pressure necessary to induce a given panel center deflection to the point of failure. In this case, the panel VDL-3 tested exhibited more center deflection and fractured sooner than the VDL-1 panel.

Figure 9:
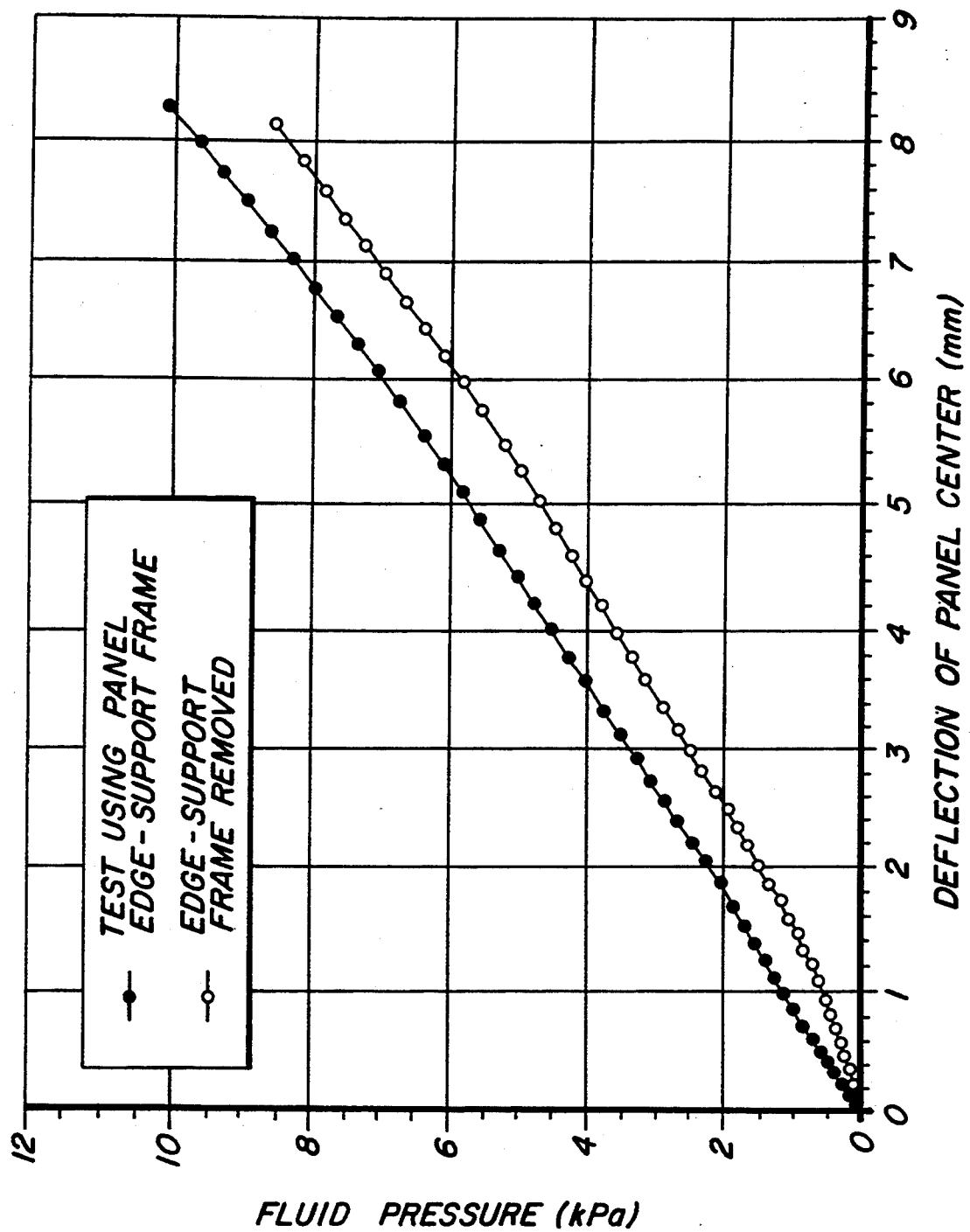
FIG. 9 is a similar view comparing the different results obtained when a panel was tested when its edge was restrained, and when unrestrained.

FIG. 9 illustrates the difference when a test panel of the same material was tested using panel edge support frame journal 31 in one instance, and not using it in another. As FIG. 9 demonstrates, true readings cannot be obtained with the panel edge support frame 31 removed.

THE OPERATION

Figure 3:
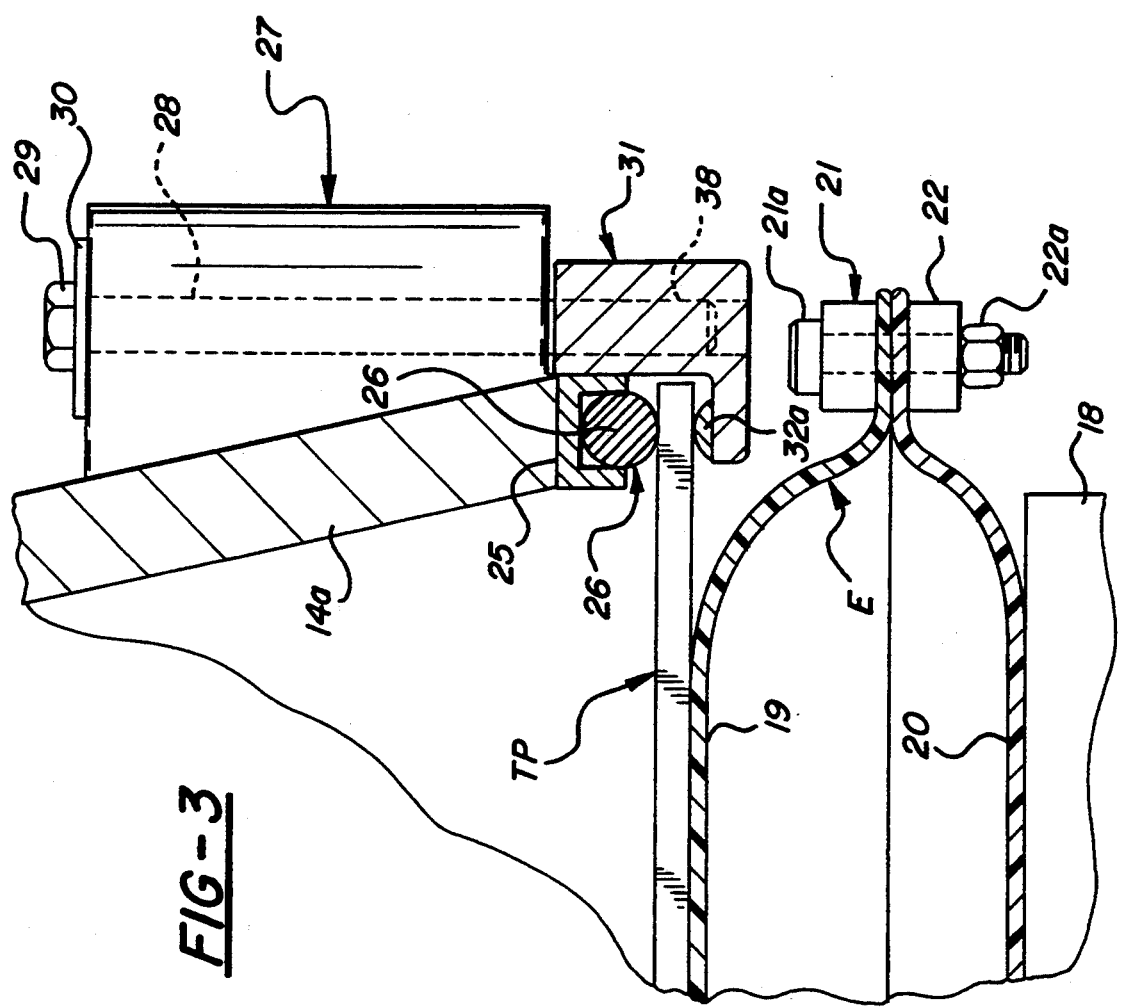
FIG. 3 is a greatly enlarged, fragmentary, elevational view showing a test panel in position ready for commencement of the test.

In practice, with a predetermined volume of water housed in the envelope E, MTS machine actuator plate 17 is moved upwardly from the positions shown in FIGS. 1 and 3 to induce a compound bend in two directions in the test panel TP. Initially, the test panel TP is only in a state of "line contact" at the edges of the panel TP, and no clamping force is exerted by the bolts 29 which would induce stresses in the panel TP. When the actuator plate 17 is moved upwardly, the pliant upper wall 19 of the envelope E assumes the shape of the panel TP, as shown by the chain lines 19' in FIG. 1 and in FIG. 3. When the actuator plate 17 begins to press the envelope against the lower surface of the test panel, the water inside will adjust so that the applied load is transferred evenly to effectively all of the exposed panel area.

The envelope is sufficiently elastic to conform throughout a broad range of panel deflection to the surface of a panel as it is forced from its original planar geometry into a compound curve, and has proved to be consistent with respect to the way applied load affects the pressure of the liquid in the envelope E.

As the actuator plate 17 is moved upwardly at a controlled rate of speed, the envelope E supplies a widely distributed pressure to the test panel TP and the bulge produced raises the core probe 39. At the same time, the pressure in envelope bladder E is increasing and this increase of pressure is linearly sensed by the pressure sensor device 24. It is, with the linear values recorded by the elements 24 and LVDT, that the graphs of FIGS. 8 and 9 may be plotted, with the readings taken at chosen intervals. The LVDT device has the capability of measuring the displacement of the panel center from its initial position to the nearest three thousandths of a millimeter.

After completion of the test, actuator plate 17 is lowered and the bolts 29 are backed off sufficiently so that the frame 31 releases. It is placed in a position of rest for unloading on a plywood plate placed on top of the envelope E. The test panel TP is removed and a new test panel TP may be placed on the support frame 31, with its edges resting on the journal system provided by members 32b and 33b. With the hydraulic actuator plate 17 on the test machine then activated to raise journal frame 31, the new test panel TP moves into contact with the frame formed by journals 26, without exerting a clamping pressure thereon. At this point, the bolts 29 in the openings 28 in the corner blocks 27 are tightened down in the threaded openings 38 just sufficiently to keep the panel TP in contact with the rods 26. Then the actuator plate 17 is lowered to remove the plywood support placed on the envelope E.

The test results portrayed in FIGS. 8 and 9 are of the stroke-controlled ramp type wherein the actuator plate 17 is commanded to move by the computer, based on the exact specification of its position at any time. The data portrayed was obtained by programming the actuator plate 17 to move upward from its initial position at the constant rate of 2.54 millimeters per minute. The pressure transducer 24 monitored the magnitude of the fluid pressure and, hence, the approximate surface pressure impinging on the surface of the test panel under test loading. To obtain the reading, the load cell pressure and LVDT channel were sampled by the data acquisition system every ten seconds, so that a pressure versus deflection curve could be plotted after the test. The test was allowed to continue until failure, which was audibly signaled. When the test was over, the specimens were examined to assess the dominant failure mode. In the case of panels VDL-1 and VDL-3, examination revealed apparent rolling shear failure occurring in the hardwood veneer facings on the tension side of these test panels, which had balsa-cores.

It is to be understood that what is termed load-controlled classical fatigue testing can also be performed on the machine. Classical fatigue refers to constant load amplitude fatigue testing, where the load function is sinusoidal. In this type of testing, a peak load test below the failure load is repeatedly applied after an initial stroke-controlled ramp test, and then the load versus deflection ramp test is repeated to determine if the specimen panel has lost some of its original stiffness. This procedure can be repeated over a large number of cycles to directly compare a broad spectrum of sandwich composites in an efficient and cost effective manner, The objective of such testing is to investigate the effect of repeated low pressure load cycles on the stiffness of the panel.

A widespread variety of test specimens can be compared with the present testing fixture assembly wherein the envelope E and edge support frame 31 are used in combination. Sandwich composite materials having delicate load density cores can be directly compared with the more traditional materials such as plywood.

It is to be understood that the embodiments described are exemplary of various forms of the invention only and that the invention is defined in the appended claims which contemplate various modifications within the spirit and scope of the invention.

I claim:

1. In a testing fixture assembly for inducing a compound bend deflection in and investigating the effects of various pressure loadings on a panel being tested which has opposing inner and outer flat sides bounded by a perimetrical edge bordering perimetrically adjacent edge portions on said flat sides, in a testing machine having a support frame element opposite a platen, which is relatively movable with respect to the support frame element from a first relatively spread position to a second more closed position, the combination which includes:
    (a) a self-contained, liquid-filled bladder, formed of a pliant, somewhat elastic material, adapted to be received on the platen for engaging an outer flat side of the said panel being tested and deflecting said panel being tested when the platen and support frame element are moved relatively to said second position;
    (b) a panel holder adapted to be supported by the frame element at a spaced distance from the platen and bladder and incorporating a pair of centrally open, spaced apart, continuously extending edge movement restraint members for receiving the panel to be tested between said pair of restraint members, the restraint members providing opposed perimetrical surfaces for contacting said edge portions on both flat sides of the said panel being tested adjacent said panels being tested's perimetrical edge and completely around both flat sides of the panel being tested; and
    (c) a measuring device having a deflection measuring element supported by said support frame element for measuring the deflection induced in said panel being tested perimetrically inboard of said panel's perimetrical edge by the bladder upon said relative movement of the platen and support frame element to said second position.

2. The apparatus of claim 1 wherein a transducer pressure sensor mechanism monitors the pressure of the liquid in said bladder during the deflection of said panel.

3. The apparatus of claim 1 wherein said panel holder includes a pyramidal structure incorporated with said support frame element, said restraint member surfaces comprising panel-contacting curvilinear cross-section journal members projecting from said pyramidal structure to form a first closed rectangular journal frame which functions as an upper panel edge portion movement restraint member and a second journal frame including interfitting side and end bars fixed on said panel holder opposite said first journal frame, with each of the interfitting side and end bars having curvilinear cross-section journal members which function as a lower panel edge portion support and movement restraint member.

4. The apparatus of claim 3 wherein said journal members forming the first closed rectangular frame comprise rods of cylindrical cross-section, and said pyramidal structure has recesses partially receiving said rods so that only said rods are contacted by the said panel being tested; said side and end bars have inwardly projecting shelves; and said journal members on said second journal frame comprise rods of cylindrical cross-section projecting above said shelves to contact the panel.

5. The apparatus of claim 1 wherein said measuring device includes a linear, variable, differential transducer having a depressible probe in contact with the center of said inner flat side of the panel being tested.

6. The apparatus of claim 1 wherein a load measuring cell mounted on said frame supports said panel holder.

7. A method of investigating the effects of various distributed pressure loadings on marine hull and other plate panels having opposing first and second flat sides bounded by a perimetrical edge bordering adjacent edge portions on said flat sides in a testing machine for inducing a compound blend deflection in a panel being tested and having a frame opposite a platen which is relatively movable toward and away from the frame, a liquid-filled self-contained bladder formed of a pliant, somewhat elastic material, adapted to be received on the platen for engaging said first side of a panel being tested and deflecting said panel being tested upon said relative movement of the platen toward said frame, a fixture supported by the frame incorporating continuously extending edge movement restraint journal frames for receiving and contacting said adjacent edge portions of the flat sides of the panel being tested perimetrically inboard and adjacent the panel being tested's perimetrical edge around both sides of the panel being tested, and a measuring device for measuring the deflection of said panel perimetrically inboard of said edge portions of the flat sides of the panel being tested as the bladder is moved with the platen and pliantly conforms to the panel being tested to apply a distributed load thereto; the steps of:
    (a) mounting the panel to be tested between said journal frames with said edge portions of the flat sides of the panel to be tested contacted around the entire perimetrical edge of the panel to be tested; and
    (b) moving said platen at a controlled rate of speed to cause the bladder to pliantly conform to the said first side of the panel being tested and apply a distributed load to said panel being tested progressively imposing a bend in the said panel being tested perimetrically inboard of said edge portions of the panel being tested in two dimensions along two axes simultaneously, while measuring the amplitude of the said deflection of said panel being tested with said measuring device.

8. The method of claim 7 including the step of recording the pressure of the liquid in said bladder and comparing the pressure with the amplitude of said deflection measured by said measuring device as said deflection is progressively imposed.

9. The method of claim 7 wherein step (b) is carried out until rupture of the panel being tested occurs.

10. The method of claim 7 wherein said journal frames include a releasable lower journal frame and the following additional steps are performed:
    (a) said platen and bladder are backed off and said lower journal frame is released from said fixture;

(b) a replacement panel to be tested and having first and second flat sides bounded by a perimetrical edge bordering adjacent edge portions of said flat sides of the replacement panel is placed on said lower journal frame;

(c) said lower journal frame is reattached to said fixture with the replacement panel disposed between said journal frames and the first and second sides of said replacement panel are only lightly contacted around the entire perimetrical edge of the replacement panel; and (d) moving said platen at a controlled rate of speed to cause the bladder to pliantly conform to the said first side of the replacement panel and apply a distributed load thereto progressively imposing a bend in the replacement panel inboard of said edge portions of said replacement panel in two dimensions along two axes simultaneously, while measuring the amplitude of the deflection of said replacement panel.

11. A testing system for inducing a compound bend deflection in and investigating the effects of progressively imposed pressure loading on a panel to be tested having opposing upper and lower generally flat sides bounded by a perimetrical edge bordering perimetrically adjacent edge portions of said generally flat sides comprising:

(a) a machine frame;

(b) a support frame element thereon;

(c) a platen mounted on said machine frame for relative vertical movement with respect to the support frame element from a first relatively spread position to a second more closed position;

(d) a self-contained, liquid-filled bladder, formed of a pliant, somewhat elastic material received on the platen for the purpose of engaging the lower generally flat side of a panel being tested inward of said perimetrical edge of the panel being tested and deflecting said panel being tested when the platen is moved relatively to said second position;

(e) a panel holder supported by the frame element and incorporating a pair of centrally open, vertically spaced apart, continuously extending, edge movement restraint members for receiving the panel to be tested between said pair of restraint members, the restraint members comprising panel-contacting, curvilinear cross-section journal members forming a first closed journal frame which functions as a restraint member for the said perimetrically adjacent edge portions of the upper generally flat side of the panel, and a second journal frame, including side and end bars fixed on said panel holder opposite said first journal frame, with each of the side and end bars mounting continuously extending, upstanding, curvilinear cross-section journal members which function as a support and movement restraint for the said perimetrically adjacent edge portions of the lower generally flat side of the panel being tested; and (f) a measuring device for measuring the amplitude of deflection induced in said panel being tested by the bladder upon said relative movement of the platen with respect to the support frame element to second position.

* * * * *